US00PP20144P2

(12) United States Plant Patent
van der Spek

(10) Patent No.: US PP20,144 P2
(45) Date of Patent: Jun. 30, 2009

(54) ***HYDRANGEA* PLANT NAMED 'SIDASHE'**

(50) Latin Name: *Hydrangea macrophylla*
Varietal Denomination: Sidashe

(76) Inventor: Daniel van der Spek, Nieuwkoopseweg 45, 2631 PP Nootdorp (NL)

( * ) Notice: Subject to any disclaimer, the term of this patent is extended or adjusted under 35 U.S.C. 154(b) by 0 days.

(21) Appl. No.: 11/903,267

(22) Filed: Sep. 22, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
*Assistant Examiner*—Louanne C Krawczewicz Myers

(57) ABSTRACT

A new and distinct *Hydrangea* cultivar named 'Sidashe' is disclosed, characterized by pink flowers with dark pink margins and a creamy white center. The new variety is a *Hydrangea*, and naturally blooms from April through September.

1 Drawing Sheet

Latin name of the genus and species: *Hydrangea macrophylla.*
Variety denomination: 'Sidashe'.

BACKGROUND OF THE INVENTION

The new cultivar is a product of a planned breeding program. The intent of this breeding program is to produce stronger pot plant varieties with attractive flower colors. The new variety was discovered as a seedling within the planned breeding program. This seedling is a result from the crossing of the female parent, an undistributed proprietary variety referred to as 9773 with the male parent, an undistributed proprietary variety referred to as 9742. The crossing was made by the inventor, Daniel van der Spek in the summer of 1999. 'Sidashe' was selected by Daniel van der Spek in May of 2001 in Nootdorp, The Netherlands.

Asexual reproduction of the new cultivar 'Sidashe' by vegetative cuttings was performed in Nootdorp, the Netherlands and has shown that the unique features of this cultivar are stable and reproduced true to type through 6 successive generations.

SUMMARY OF THE INVENTION

The cultivar 'Sidashe' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sidashe'. These characteristics in combination distinguish 'Sidashe' as a new and distinct *Hydrangea* cultivar:

1. Flattened inflorescence;
2. Unique petal coloration of pink with dark pink margins and a creamy white center;
3. Dark green foliage;
4. Strong plant, resisting breaking in production and post-harvest situations.

Plants of the new cultivar 'Sidashe' are similar to plants of the female parent, '9773' in most horticultural characteristics, however, plants of the new cultivar 'Sidashe' differ from '9773' in the following characteristics;

1. Foliage color of 'Sidashe' is green whereas '9773' is green with purple margins.
2. 'Sidashe' has more flowers per inflorescence.
3. 'Sidashe' has a wider inflorescence.

Plants of the new cultivar 'Sidashe' are similar to plants of the male parent, '9742' in most horticultural characteristics, however, plants of the new cultivar 'Sidashe' differ from '9742' in the following characteristics;

1. Flower color of 'Sidashe' is pink with dark pink margins and a creamy white center whereas '9742' has solid pink flowers.
2. 'Sidashe' is a taller plant.

Plants of the new cultivar 'Sidashe' are similar to plants of the commercial variety 'Paris Rapa,' U.S. Plant Pat. No. 10,906. However, plants of the new cultivar 'Sidashe' differ from 'Paris Rapa' in the following characteristics;

1. Foliage of 'Sidashe' is much more resistant to stress than 'Paris Rapa'.
2. 'Sidashe' has a wider inflorescence than 'Paris Rapa'.
3. 'Sidashe' flowers are darker red.
4. 'Sidashe' plants are taller than 'Paris Rapa'.
5. 'Sidashe' plants produce roots faster than 'Paris Rapa'.

BRIEF DESCRIPTION OF THE PHOTOGRAPH

The accompanying photograph in FIG. 1 illustrates in full color a typical blooming plant of 'Sidashe' grown in a greenhouse. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'Sidashe' plants grown in a greenhouse in Brielle, The Netherlands from October 2005 to October 2006. The growing temperature ranged from 16° C. to 17° C. at night to 18° C. to 20° C. during the day. The pH of the growing medium was between 5.0 and 5.5. Measurements and numerical values represent averages of typical flowering types.

Botanical classification: *Hydrangea macrophylla* cultivar 'Sidashe'.

PROPAGATION

Time to Rooting: 19 to 21 days at approximately 20° C.
Root Description: Fine, fibrous.

PLANT

Growth Habit: Flowering perennial shrub.
Height: Approximately 44 cm from soil level to the top of the inflorescence.
Blooming period: Naturally blooming April through September.
Plant Spread: Approximately 56.5 cm.
Growth Rate: Moderate to vigorous.
Branching Characteristics: Moderately free branching.
Length of Lateral Branches: Approximately 32.1 cm.
Number of Lateral Branches: Approximately 12.
Diameter of Lateral Branches: Approximately 0.6 cm.
Pinching Required: Yes.
*Details of pinching.*—The first pinch is given at 8 weeks from the planting of a rooted cutting. A second pinch is given 12 weeks from planting a rooted cutting.
Lateral Branch Shape: Round.
Lateral Branch Strength: Very strong.
Lateral Branch Texture: Leathery.
Lateral Branch Color: Approximately RHS Yellow-Green 144A, slightly tinged at the nodes with RHS Greyed-Purple 183D.
Other Stem or Plant Characteristics: Stems covered with lenticels at a density of approximately 5 lenticels per square cm.
*Lenticel length.*—Approximately 0.25 cm.
*Lenticel width.*—Approximately 0.075 cm.
*Lenticel color.*—About RHS Greyed-Purple 183D.
Number of Leaves per Lateral Branch: Average 8.
Age of Plant Described: Approximately 1 year.

FOLIAGE

Leaf:
*Arrangement.*—Opposite.
*Compound and or single.*—Single.
*Average length.*—Approximately 12.3 cm.
*Average width.*—Approximately 7.1 cm.
*Shape of blade.*—Broad oval to broad elliptic oblong.
*Apex.*—Apiculate
*Base.*—Acuminate.
*Attachment.*—Stalked.
*Margin.*—Serrate, approximately 3 teeth per cm.
*Texture of top surface.*—Moderately glossy, non-pubescent.
*Texture of bottom surface.*—Matte, non-pubescent.
*Leaf internode length.*—Approximately 6.3 cm.
*Color.*—Young foliage upper side. Near R.H.S. Green 146B. Young foliage under side. Near R.H.S. Green 138B. Mature foliage upper side. Near R.H.S. Green 139B. Mature foliage under side. Near R.H.S. Green 138B.
*Venation.*—Type: Pinnate. Venation color upper side: Near R.H.S. Yellow-Green 145A. Venation color under side: Near R.H.S. Yellow-Green 145B.
*Durability of foliage to stresses.*—High.
Petiole:
*Average length.*—Approximately 3.2 cm.
*Diameter.*—Approximately 0.4 cm.
*Color.*—Near R.H.S. Yellow-Green 145B.

FLOWER

Bloom Period:
*Natural season.*—Continuous April through September.
Inflorescence:
*Arrangement.*—Terminal.
*Type.*—Flattened compound corymb.
*Height.*—Approximately 8.2 cm.
*Width.*—Approximately 17.0 cm.
*Quantity of flowers per inflorescence.*—Fertile flowers, approximately 17. Sterile Flowers, approximately 230.
Bud:
*Bud shape* (*sterile flowers*).—Obovate.
*Bud length* (*sterile flowers*).—Approximately 0.5 cm.
*Bud diameter* (*sterile flowers*).—Approximately 0.3 cm.
*Bud color* (*sterile flowers*).—Near R.H.S. Red 54C, top darker, Red 54B. Base/calyx: Near R.H.S. Yellow-Green 144C.
*Bud shape* (*fertile flowers*).—Globose.
*Bud length* (*fertile flowers*).—Approximately 0.5 cm.
*Bud diameter* (*fertile flowers*).—Approximately 0.5 cm.
*Bud color* (*fertile flowers*).—*Near RHS Yellow-Green* 145A with top of bud near RHS Red-Purple 63B. Fertile flowers do not open.
Flower:
*Characteristics.*—Only sterile flowers fully open, fertile flowers shrivel and do not open.
*Shape.*—Rotate.
*Facing direction.*—All directions, with the majority facing outward.
*Quantity flowers per lateral stem.*—Approximately 250.
*Quantity of flowers and buds per plant.*—Approximately 2000.
*Diameter of entire flower.*—Fertile; Approximately 1.2 cm. Sterile: Approximately 4.1 cm.
*Depth of flower.*—Fertile; Approximately 0.7 cm. Sterile: Approximately 2.2 cm.
*Rate of opening.*—Individual flowers: Fully open approximately 5 days from the bud stage. Whole Plant: Approximately 50% of flowers open at once.
*Flower longevity on plant.*—Fertile flowers: Approximately 5 days. Sterile flowers: Approximately 35 days.
*Persistent or self-cleaning.*—Persistent.
*Fragrance.*—No.
Petals:
*Length of petal.*—Approximately 4.8 cm.
*Width of petal.*—Approximately 2.8 cm.
*Apex.*—Acute.
*Base.*—Cordate.

*Shape of petal.*—Ovate.
*Petal margin.*—Entire.
*Petal arrangement.*—Rotate.
*Petal number.*—Average 5.
*Petals fused.*—No.
*Petal appearance.*—Dull.
*Petal texture* (*both surfaces*).—Smooth.

Color:
*Upper surface at first opening.*—Near Red-Purple 58D, top margin near Red-Purple 58B,
*Upper surface at maturity.*—Near Red-Purple 58C, top margin near Red-Purple 58B, base near 58D.
*Upper surface at fading.*—Near Red-Purple 58B.
*Under surface at first opening.*—Near Red-Purple 58D, top margin near Red-Purple 58B, base near Red-Purple 58D.
*Under surface at maturity.*—Near Red-Purple 58C, top margin near Red-Purple 58B, base near 58D.
*Under surface at fading.*—Near Red-Purple 58B.

Petaloids: No.
Fragrance: None.

CALYX

Present: Yes.
Shape: Rotate, lower ¾ fused.
Length: Approximately 0.35 cm.
Diameter: Approximately 1.35 cm.

SEPAL

Sepals: Only sterile flowers have sepals. Fertile flowers shrivel and do not open.
Number: Average 5.
Sepal Texture (both surfaces): Smooth.
Sepal Arrangement: Rotate.
Sepal length: Approximately 0.4 cm.
Sepal width: Approximately 0.1 cm.
Sepal shape: Deltoid.
Base: Fused into a tube ⅔ of length.
Apex shape: Acute.
Margin: Entire.
Color: Upper side near R.H.S. Yellow-Green 144C. Under side near R.H.S. Yellow-Green 144C, base Yellow-Green 144D.

PEDUNCLE

Length: Approximately 4.2 cm.
Diameter: Approximately 0.35 cm.
Angle: Approximately 30 degrees (0 degrees=straight upright).
Strength: Strong.
Color: Near R.H.S. Yellow-Green 144B.

PEDICEL

Present: Yes.
Length (sterile flowers): Approximately 0.9 cm.
Diameter (sterile flowers): Approximately 0.1 cm.
Angle (sterile flowers): Approximately 10 degrees.
Strength (sterile flowers): Strong.
Color (sterile flowers): Near White 155A, base Greyed-Purple 187D.
Length (fertile flowers): Approximately 0.7 cm.
Diameter (fertile flowers): Approximately 0.3 cm.
Angle (fertile flowers): Approximately 10 degrees.
Strength (fertile flowers): Moderate.
Color (fertile flowers): Near Yellow-Green 145C.

REPRODUCTIVE ORGANS

*Number of pistil per flower:* 3.
*Pistil length.*—Approximately 0.25 cm.
*Stigma shape.*—Lobed.
*Stigma color.*—Near Red-Purple 57D.
*Style colors.*—Near Red-Purple 62D.
*Style length.*—Approximately 0.2 cm.
*Ovary color.*—Near Yellow-Green 154C.
*Stamens.*—Average 10.
*Anther shape.*—Broad kidney-shaped.
*Anther size.*—0.15 cm.
*Anther color.*—Near White 155A, filament colored Red-Purple 62C.
*Pollen color.*—Near White 155A.
*Pollen quantity.*—Very low.

OTHER CHARACTERISTICS

Disease Resistance: Neither resistance nor susceptibility to diseases or pests has been observed in this variety.
Drought Tolerance and Cold Tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.
Fruit/Seed Production: No fruits/seeds detected to date.

What is claimed is:

1. A new and distinct cultivar of *Hydrangea* plant named 'Sidashe' as herein illustrated and described.

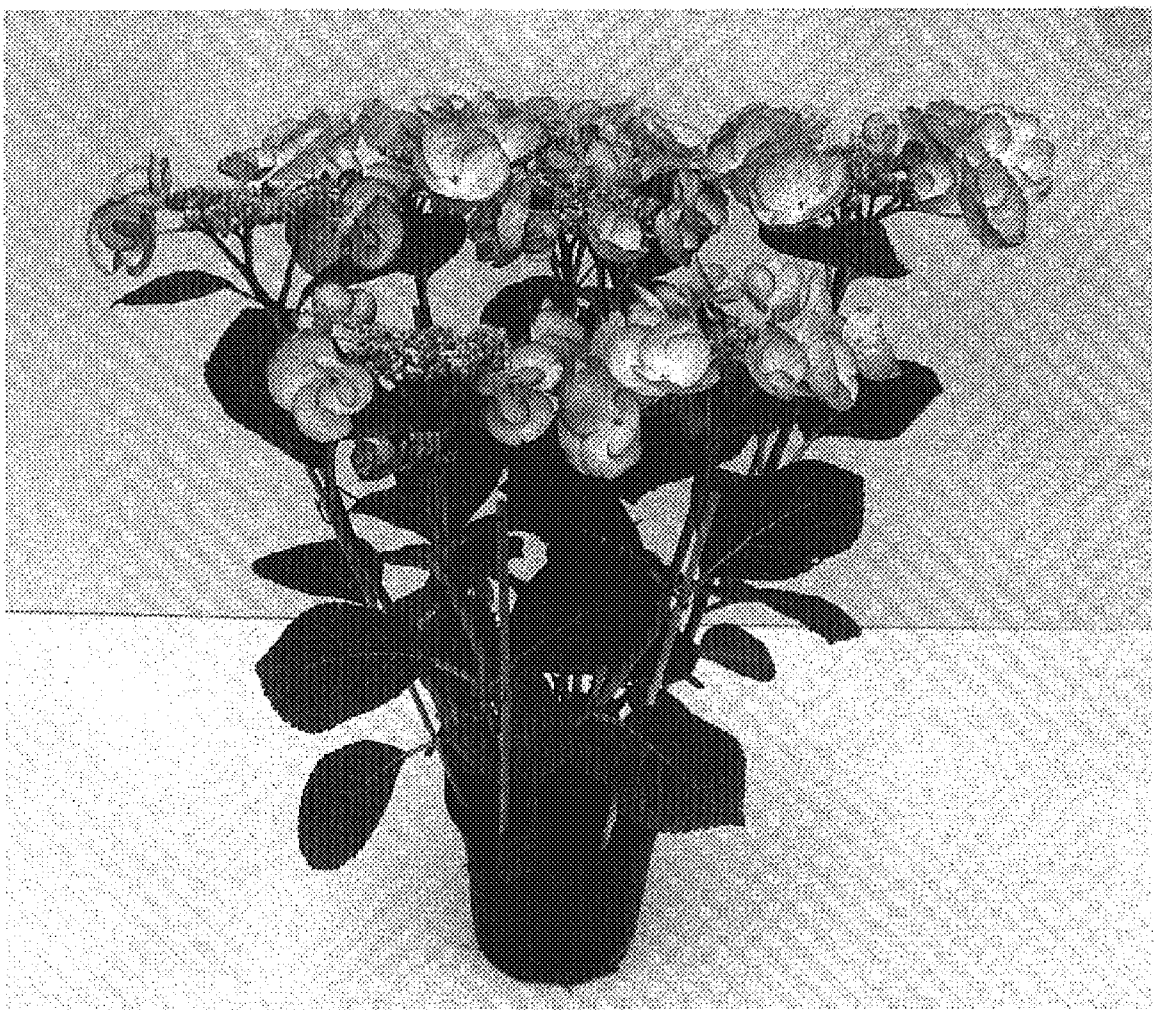

* * * * *